March 13, 1973 O. RIEGER Plant Pat. 3,317
BEGONIA PLANT
Filed June 30, 1971
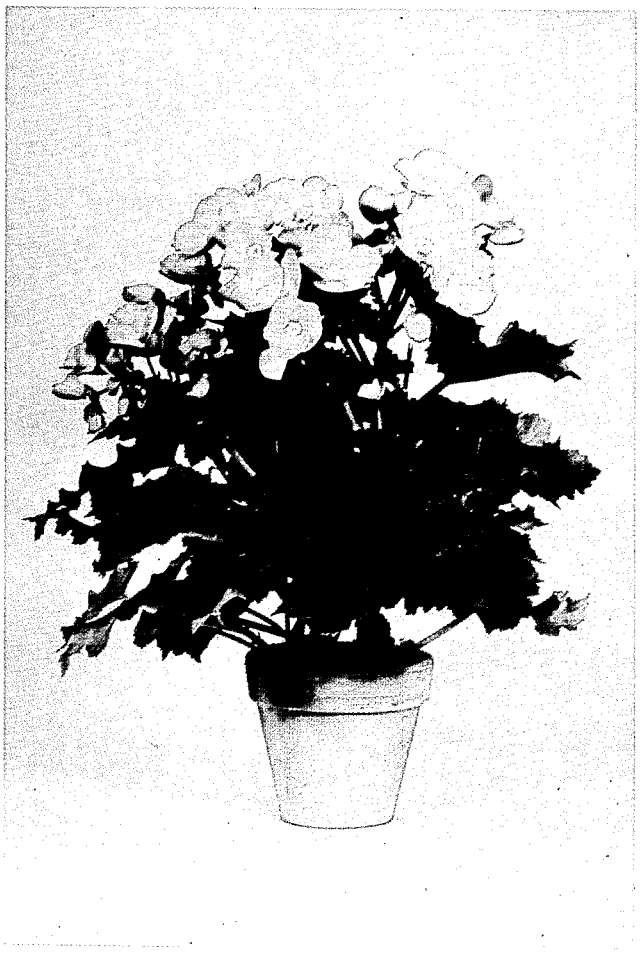

United States Patent Office

Plant Pat. 3,317

Patented Mar. 13, 1973

3,317
BEGONIA PLANT

Otto Rieger, deceased, by Gertrud Rieger, legal representative, Nurtingen, Germany, assignor to Mikkelsens, Inc., Ashtabula, Ohio Filed June 30, 1971, Ser. No. 158,643
Int. Cl. A01h 5/00
U.S. Cl. Plt.—68 1 Claim The present invention relates to a new and distinctive variety of begonia plant, botanically known as *Begonia elatior*, discovered by me in a nursery in Nurtingen, Germany, as a mutation of an unpatented hybrid developed by me through controlled breeding. Asexual reproduction by stem and leaf cuttings has reproduced the unique features of the new variety through successive propagations.

The following characteristics distinguish the new begonia from both its parent and other begonias commercially known and used in the floriculture industry:

(1) Plants are of a short, squatty growth with close internodes.

(2) The flowers are almost exclusively masculine, single with a slight tendency to doubleness. When flowers are double, the inner petals are yellowish.

(3) The new variety is very floriferous, usually covering the entire outer area of the plant.

(4) The flower stems are short and strong. The bloom size is up to 6 cm. in diameter.

(5) The bloom color is a deep dark shining red. The color is more intense than in Rieger's Schwabenland, a well established predominant variety in the European markets.

(6) Individual blooms have extremely good keeping qualities; this, coupled with an abundance of blooms, provides superior floral characteristics.

(7) Leaves are heart shaped, hard and pointed. The leaf edge is wavy and strongly indented. Leaf color is generally a dark glossy green.

(8) The new variety propagates well from leaf cuttings. This is of economic importance in that the leaf cuttings develop rhizomatous shoots and produce a full plant.

(9) The overall growth of the new variety is somewhat weaker than Rieger's Schwabenland, and temperature requirements are higher, with this last feature being an advantage for summer cultivation in northern latitudes. Blooming season is from spring to autumn.

The accompanying colored photograph illustrates the overall appearance of this variety taken as a face view of the plant and showing the colors as true as it is reasonably possible to obtain in a colored reproduction of this type.

The following is a detailed description of my new begonia variety based on plants produced under commercial practices in Nurtingen, Germany. Color references are made to the Royal Horticultural Society Colour Chart except where general color terms of ordinary dictionary significance are used.

Parentage: Mutation from a hybrid resulting from crossing a mutant of *Begonia bertini compacta* as a seed parent with *Begonia socotrana* as a pollen parent.

Propagation: Continuous and successive vegetative propagation and subsequent flowering of leaf cuttings and stem cuttings indicates that the mutation is stable and reproduces true to type.

Rooting habit: Rooting is average for begonias. Development of rhizomatous growths from leaf cuttings is excellent.

Form: Plants are semi-dwarf, compact, and self-branching with close internodes. Leaf cuttings produce full bodied specimen plants.

Habit of growth: Vigorous, upright, with some support required under poor growings conditions. Does not grow well under dull conditions of winter season.

Blooming habits: Flowers are usually single with slight tendencies to doubleness. Blooms are normally carried in trusses; the number of blooms vary with the age of the plant and the time of year when flowering.

Blooming season: The new variety can be flowered any season of the year by appropriate greenhouse cultural practices. The best quality flowering plants are produced under long days and high temperature conditions of the summer season.

Foliage: Alternate; borne at a close angle to the stems; persistent; slightly above average in quantity. Foliage is very hard and typically drawn to a point.

*Size.*—Small to medium approximately 7 to 12 cm. long and 5 to 8 cm. wide. Environmental and general plant conditions can greatly alter the size and color of foliage.

*Shape.*—Oval pointed, heart shaped.

*Texture.*—Upper side—leathery, glossy; under side—smooth, highly reflective.

*Margin.*—Indented and wavy.

*Color.*—Upper side—nearly RHS 135 A to B; under side—nearly RHS 138 B.

Disease resistance: Resistance of the foliage against mildew is quite extensive as tested under normal growing conditions in the presence of other begonias susceptible to mildew.

Flowers:

*Borne.*—On trusses with several to a stem in regular clusters. Individual blooms have above average keeping qualities. Petals average 4–6 per bloom with occasional doubling. Petals at maturity are nearly flat and measure up to 6 cm. across the face. Flowers are male, showing bright yellow stamens and anthers in the center eye.

*Quantity.*—Very floriferous with continuous flowering over a relatively long period of time.

*Buds.*—Develop progressively at the nodes to the size of a flat coin approximately 2 cm. in diameter before starting to open. The lighter reverse side of the petals is seen at this time.

*Petals.*—Nearly RHS 43 A.

*Reproductive organs.*—Stamens—quite profuse. Color RHS 7 A when young to RHS 23 A at maturity. Pollen—Color RHS 7 A. Styles/ovaries—none seen to date.

What is claimed:

1. A new and distinct variety of begonia characterized particularly by its short squatty growth, with close internodes, its masculine flowers, its very floriferous habit, its short and strong stems, its deep dark shining red blooms which have superior keeping qualities, its heart shaped and pointed leaves, and its ease of propagation from leaf cuttings; and particularly distinguished from the variety Rieger's Schwabenland by its deeper red blooms, its shorter compact growth and its hard, pointed foliage.

No references cited.

ROBERT E. BAGWILL, Primary Examiner